United States Patent [19]

Sularz

[11] Patent Number: 4,971,271
[45] Date of Patent: Nov. 20, 1990

[54] ARTICLE ORGANIZER AND HOLDER ASSEMBLY

[76] Inventor: Frank D. Sularz, 2091 Sussex La., Colorado Springs, Colo. 80909

[21] Appl. No.: 347,665

[22] Filed: May 5, 1989

[51] Int. Cl.⁵ .............................................. F16M 13/00
[52] U.S. Cl. ..................................... 248/68.1; 248/73; 248/74.2; 248/222.2
[58] Field of Search ................. 248/68.1, 222.2, 220.2, 248/73, 74.2; 5/498; 24/16 R; 128/DIG. 6

[56] References Cited

U.S. PATENT DOCUMENTS

| | | | |
|---|---|---|---|
| D. 190,429 | 5/1961 | Hoagland | 248/68.1 X |
| 2,739,320 | 3/1956 | Kostka | 5/498 X |
| 2,988,759 | 6/1961 | Gerdes | 5/498 |
| 3,696,920 | 10/1972 | Lahay | 128/DIG. 26 X |
| 4,579,310 | 4/1986 | Wells et al. | 248/68.1 X |
| 4,655,424 | 4/1987 | Oshida | 248/68.1 X |
| 4,705,244 | 11/1987 | Saotome et al. | 248/68.1 |

Primary Examiner—Ramon O. Ramirez
Attorney, Agent, or Firm—Phillip A. Rein

[57] ABSTRACT

This invention relates to an article organizer and holder assembly having (1) a main support base; (2) an article receiver and retainer assembly mounted on the support base; and (3) a connector means having a pair of clip members each attached to respective outer ends of the main support base for attachment to a medical patient's bed sheet or the like. The article receiver and retainer assembly includes a main support block member having a plurality of independent article support sections, each adapted to receive and hold a tube member therein to prevent axial and lateral movement thereof. Each independent article support section is provided with a main body sectio having a connector slot section cut therein. The connector slot section is of generally J-shape in transverse cross section and having a spiral slot portion integral with a connector hole portion. The connector slot section is operable to receive, enclose, and temporarily anchor a respective tube member therein. A plurality of tube members are operable to be held within respective ones of the independent article support sections in an adjacent parallel condition.

8 Claims, 1 Drawing Sheet

U.S. Patent   Nov. 20, 1990   4,971,271
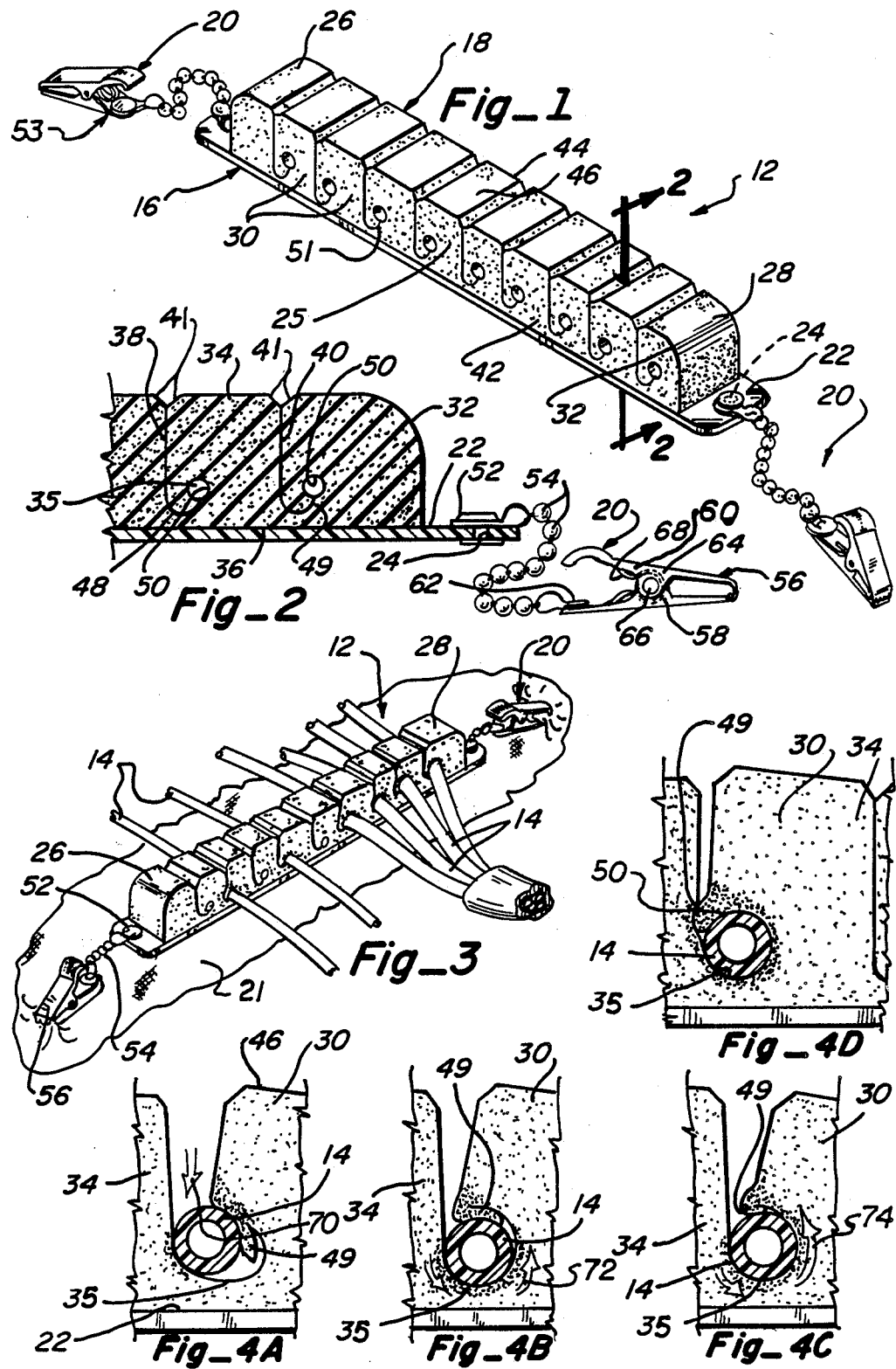

4,971,271

ARTICLE ORGANIZER AND HOLDER ASSEMBLY

PRIOR ART

A patent search on this invention revealed the following U.S. Patents:

| U.S. Pat. No. | Invention | Inventor |
| --- | --- | --- |
| 2,727,513 | INFUSION NEEDLE SUPPORT | Herman Muller |
| 3,210,816 | SURGICAL CLAMP | Bette Jean Clemons |
| 3,368,564 | TUBE ANCHOR AND GUIDE DEVICE | Richard C. Selix |
| 3,696,920 | DEVICE FOR ORGANIZING OBJECTS | Charles A. Lahay |
| 4,029,103 | ANCHORING PLATE FOR MEDICAL TUBES | Francis P. McConnell |
| 4,336,806 | MEDICAL TUBING HOLDER | John Eldridge, Jr. |
| 4,605,397 | APPARATUS FOR SUPPORTING AND MANAGING A MEDICAL PIG TAIL TYPE FLUID INFUSION DEVICE | Ligon et al |
| 4,606,735 | MEDICAL TUBING HOLDER | Wilder et al |
| 4,702,736 | UNIVERSAL CLAMP | Kalt et al |

The Lahay patent discloses a device for organizing objects as best illustrated in FIG. 5 having (1) an outer enclosure for sealing in a sterile condition (2) a semi-rigid foam block structure having a plurality of circular openings and V-shaped grooves leading from a top surface to the circular openings; and (3) a means for attaching to a support surface such an adhesive backing.

The McConnell patent discloses an anchoring plate for medical tubes including a foam type structure having circular openings to receive tube members therein and slits leading to the subject openings. This device provides a means for holding tube members in a curved condition and can be attached to the patient by a belt member.

The Ligon et al patent discloses an apparatus for supporting and managing fluid infusion devices and teaches the use of alligator clips for attaching same to bed linen or the like.

The Eldridge, Jr. and Kalt et al patents disclose tubing holder structures with one utilizing magnet structures and the other using velco connectors.

The Clemons, Wilder et al, and Selix patents disclose V-shaped clamp structure to receive tube members therein but are not deemed pertinent to our invention.

The Muller patent discloses an infusion needle support which is adapted to fit about a supply tubing and attached to an arm of the patient.

PREFERRED EMBODIMENT OF THE INVENTION

In one preferred embodiment of this invention, an article organizer and holder assembly is operable to receive, engage, and hold IV (intravenous) tube members and having a connector means for releasable attachment to a bed sheet, person's garment, or the like. The article organizer and holder assembly includes (1) a main support base; (2) an article receiver and retainer assembly mounted upon the main support base; and (3) the connector means attached to opposite ends of the main support base for attachment to an adjacent area. The main support base is of a rectangular shaped retainer type plate including a main support surface and having clip anchor holes at opposite ends thereof. The article receiver and retainer assembly consists of a main support block member having end support portions integral and interconnected through independent article support sections. The independent article support sections are each adapted to receive and support a tube member therein and provided with a main body section having a connector slot section therein. Each main body section is provided with a bottom wall secured in a fixed relationship to the main support base; opposed side walls integral with the bottom wall; a front wall and a back wall interconnecting the side walls and the bottom wall; and a top wall interconnecting the front, back, and side walls to form a rectangular block shape. Each of the abutting side walls are formed with a cooperating upper tapered corner section for initially receiving and directing the tube members into the respective connector slot sections. Each connector slot section is provided with a main spiral slot section integral with a circular connector hole portion. Each sprial slot section is provided with a lip portion which is first engaged with the tube member inserted therewithin and encloses the respective tube member.

OBJECTS OF THE INVENTION

One object of this invention is to provide an article organizer and holder assembly having a plurality of independent article support sections therein to independently receive a respective tube member therein for receiving, enclosing, and holding same against axial and lateral movement.

One further object of this invention is to provide an article organizer and holder assembly including a support base with a plurality of article receiver and retainer assemblies thereon, each adapted to receive and hold a tube member therein; and having a connector means secured to opposite ends of the main support base for releasable attachment to a patient's garment, a bed sheet, or the like.

One other object of this invention is to provide an article organizer and holder assembly including (1) a main support base with a flat support surface to be readily supported on a patient's garment, bed sheet, or the like; and (2) an article receiver and retainer assembly having a plurality of article support sections, each independently adapted to receive and hold respective tube members in adjacent parallel relationship for organization and anchoring thereof which is important under medical surgical operating conditions.

Still, one further object of this invention is to provide an article organizer and holder assembly being of a compact lightweight nature; economical to manufacture; simple to use; and substantially maintenance free.

Various other objects, advantages and features of the invention will become apparent to those skilled in the art from the following discussion, taken in conjunction with the accompanying drawings, in which:

FIGURES OF THE INVENTION

FIG. 1 is a perspective view of the article organizer and holder assembly of this invention;

FIG. 2 is an enlarged sectional view taken along lines 2—2 in FIG. 1;

FIG. 3 is a perspective view of the article organizer and holder assembly of this invention illustrated as attached to a bed sheet or patient's garment and having a plurality of IV tube members connected thereto; and FIGS. 4A-D, inclusive, are schematic diagrams illustrating the steps in attaching a tube members within a connector slot section of the article organizer and holder assembly of this invention.

The following is a discussion and description of preferred specific embodiments of the article organizer and holder assembly of this invention, such being made with referenc to the drawings, whereupon the same reference numerals are used to indicate the same or similar parts and/or structure. It is to be understood that such discussion and description is not to unduly limit the scope of the invention.

DESCRIPTION OF THE INVENTION

Referring to the drawings in detail and, in particular to FIG. 1, an article organizer and holder assembly of this invention, indicated generally at 12, is utilized to hold an organize a plurality of adjacent IV tube members 14 required to be held in a spaced adjacent condition while restricting axial or lateral movement thereof. The article organizer and holder assembly 12 includes (1) a main support base 16; (2) an article receiver and retainer assembly 18 secured to the main support base 16; and (3) a connector means 20 attached to the main support base 16 and releasably connectable to a bed sheet 21 or the like.

As noted in FIG. 1, the main support base 16 is of a rectangular shape being a retainer plate having an upper main support surface 22 and clip anchor holes 24 at each opposite end of the main support base 16. The main support base 16 is preferrably constructed of a material having flexibility about its longitudinal and lateral axes in order to conform to the surface on which it is supported. The main support base 16 may be constructed of a plastic or stainless steel material which can readily conform to sterilizing requirements and health regulations for use in surgical operating room condtions.

The article receiver and retainer assembly 18 includes an elongated main support block member 25 including end support sections 26, 28 at opposite ends and integrally interconnected by a plurality of independent article support sections 30. Each end support section 26, 28 has an arcuate end portions 32 extended inwardly to an adjacent independent article support sections 30.

The independent article support sections 30 are illustrated as a plurality, namely eight (8), each identical having (1) a main body section 34; and (2) a connector slot section 35 within the main body section 34.

Each main body section 34 is of a generally block shape having (1) a bottom wall 36; (2) spaced parallel side walls 38, 40 integral with the bottom wall 36; (3) a front wall 42 integral with the bottom wall 36 and the side walls 38, 40; (4) a back wall 44 similar to the front wall 42 being integral with the bottom wall 36 and side walls 38, 40; and (5) a top wall 46 integral with the front wall 42, back wall 44, and the side walls 38, 40. It is noted that each adjacent side wall 38, 40 has a tapered corner section 41 therein to conjointly form a V-shaped slot for ease of adding the respective tube members 14 into a respective connector slot section 35 as will be explained.

Each connector slot section 35 is provided with a spiral slot portion 48 of a generally J-shaped as observed by viewing the back wall 44 and having a hole portion 50 integral with a short leg 51 of the spiral slot portion 48. The spiral slot portion 48 is provided with an integral lip portion 49 which is operable to be deformed during adding a tube member 14 thereto and eventually enclose the subject tube member 14 as will be explained.

As noted in FIG. 1, the end support section 26 has the side wall 38 having a tapered corner section 41 which cooperates with a similar tapered corner section 14 in side wall 40 of the adjacent one of the independent article support sections 30. The other end section 28 is provided with the main body section 34 having a connector slot section 35 therewithin so as to conjointly provide a total of nine (9) of the connector slot sections 35 to receive respective ones of the tube members 14 therein.

The article receiver and retainer assembly 18 is constructed of a flexible deformable material such as on elastic, rubber or, preferrably, a semi-rigid foam material operable to be readily deformed on moving a tube member 14 downwardly through the adjacent tapered corner sections 41 into a connector slot section 35 in a manner to be explained in detail.

As best noted in FIG. 2, the connector means 20 comprises two (2) attachment assemblies 53, each secured to a respective end of the main support base 16. Each includes (1) a connector member 52 mounted within a respective clip anchor hole 24; (2) a chain member 54 secured to one end of the connector member 54; and (3) a clip member 56 connected to the respective opposite ends of the chain member 54.

Each clip member 56 resembles an alligator clip having a clip base 58 with a bias clip member 60 mounted thereon. The clip base 58 includes a connector post 62 which is secured to the chain member 54. The bias clip member 60 includes a clamp section 64; a pivotal shaft 66 connected to the clamp section 64 and an upturned portion of the clip base 58; and a spring member 68 placed between the clip base 58 and the bias clip member 60 to bias the same in a clockwise direction as noted in FIG. 2 to hold in the clamped condition. It is obvious that one end of the clamp section 64 is moved downwardly towards the clip base 58 against bias of the spring member 68 to an open condition for attachment to the bed sheet 21 or a patient's garment in a conventional manner.

Although the connector assembly 20 has been illustrated as utilizing a simple ball, chain, and alligator clip structure, it is obvious that other attachment means could be utilized to hold the article organizer and holder assembly 12 of this invention against a support surface to control and restrain axial and lateral movement thereof. Other such attachment means could be used such as velcro connectors, adhesive, safety pin type structures, or the like.

USE AND OPERATION OF THE INVENTION

In the use and operation of the article organizer and holder assembly 12 of this invention, it can be readily attached to the bed sheet 21 through use of the connector means 20. Of course, it is obvious that the article organizer and holder assembly 12 can be attached to the garment of a medical patient in an operating room in such a manner as to maintain a firm support on a support surface with contact of an undersurface of the main support base 16 therewith.

On attaching IV tube members 14 to the article organizer and holder assembly 12 of this invention, a plurality of the tube members 14 can be attached thereto in a spaced adjacent relationship plus using tube members 14 of various sizes as shown in FIG. 3. It is obvious that the connector slot sections 35 can be made with variable diameters of the connector hole portions 50 to accomodate tube members 14 of different diameters.

On attachment of a tube member 14 as noted in FIG. 4A, the tube member 14 is first placed against the adjacent tapered corner sections 41 and moved downwardly therein as noted by an arrow 70. The tube member 14 can be rotated as noted by an arrow 72 in FIG. 4B which causes a subsequent movement of the lip portion 49 of the connector slot section 35. On further movement laterally and rotationally as shown by an arrow 74 in FIG. 4C, it is noted that the contact of the outer surface of the tube member 14 engages the lip portion 49 for its movement towards an enclosed condition.

As noted in FIG. 4D, the tube member 14 is completely placed within the connector hole portion 50 and having a lip portion 49 extended completely around the same. The lip portion 49 in this condition acts as a holding or latch structure to prevent vertical movement of the respective tube member 14 from the connector hole portion 50.

These steps and operation of the invention can be repeated as necessary to provide a plurality of the tube members 14 mounted in respective ones of the independent article support sections 30 as noted in FIG. 3.

It has also been found, depending on the diameter of the respective tube member 14 to the diameter of the connector hole portion 50, the tube members 14 can be inserted by forcing downwardly between the adjacent tapered corner section 41 and, due to the flexibility of the rubber foam material of the article support sections 30, will readily achieve the condition as shown in FIG. 4D.

On removing a tube member 14, it is found that merely an upward movement thereof into the connector slot section 35 will disengage it from the lip portion 49 and the connector hole portion 50. Due to the flexibility of the rubber foam material, the connector slot section 35 has a resilient memory and will return to shape and condition as noted in FIG. 2.

The article organizer and holder assembly of this invention can have the main support base constructed of a plastic or stainless steel material with the article receiver and retainer assembly using a suitable foam or rubber material so as to be readily sterilized for repeat usage thereof. In the alternative, the entire article organizer and holder assembly can be constructed of the plastic and foam material of low weight and cost so as to be readily disposed of after each usage thereof similar to syringe needles.

It is obvious that the independent article support sections can be respectfully color coded so as to immediately and visually indicate which one thereof should obtain a particular tube member therein. For example, certain colors such as red could be utilized to hold IV tube members which are transferring blood into a medical patient. The color green on article support sections could be utilized to indicate a tube member used to supply glucose and nutrients to subject medical patient. It is obvious that other color codes could be utilized with the article organizer and holder assembly of this invention to add to the organization and lessen any confusion with the multiple tube members now utilized in surgical operating rooms.

The article organizer and holder assembly of this invention is attractive in appearance; economical to manufacture; simple to use; and easy to maintain and sterilize.

While the invention has been described in conjunction with preferred specific embodiments thereof, it will be understood this description is intended to illustrate and not to limit the scope of the invention, which is defined by the following claims:

I claim:

1. An article organizer and holder assembly operable to releasably receive a tube member to be restrained against axial and lateral movement, comprising:
    (a) an article receiver and retainer assembly having an article support section; and
    (b) said article support section having a spiral slot portion of J-shape connected to a connector hole portion operable to receive a tube member therein;
    whereby the tube member is movable into said spiral slot portion and laterally into said connector hole portion to be enclosed within said article support section to hold against axial and longitudinal movement.

2. An article organizer and holder assembly as described in claim 1, wherein:
    (a) said spiral slot portion having said connector hole portion integral with a short leg of said spiral slot portion.

3. An article organizer and holder assembly as described in claim 1, wherein:
    (a) said connector hole portion of a size slightly smaller than the diameter of the tube member so as to enclose and contact same to restrict axial movement of the tube member in said connector hole portion due to frictional contact therebetween.

4. An article organizer and holder assembly operable to releasably receive one or more tube members to be held in adjacent parallel relationship and to be restrained against axial and lateral movement, comprising:
    (a) an article and receiver assembly having a plurality of adjacent cooperating article support sections constructed of a flexible material; and
    (b) said article support sections each having a spiral slot portion of J-shape connected to a connector hole portion to receive a tube member therein;
    whereby the tube member is movable into one of said spiral slot portions and laterally into said connector hole portion to be enclosed within said respective one of said article support sections to hold against axial and longitudinal movement.

5. An article organizer and holder assembly as described in claim 4, wherein:
    (a) said connector hole portion of a size slightly less than the tube member therein and, due to enclosing thereof and contact therewith, restrict the axial and longitudinal movement of the tube member due to frictional contact of the tube member with an outer surface of said connector hole portion.

6. An article organizer and holder assembly as described in claim 4, wherein:
    (a) said article support sections having outer side walls placed in abutting adjacent relationship with said side walls of adjacent ones of said article support sections; and
    (b) said spiral slot portion of a generally hook shape integral with adjacent side walls with said article support sections and having an outer arcuate portion connected to said hole portion positioned inwardly and between side walls of respective ones of said article support sections;

whereby a tube member is moved downwardly between adjacent side walls defining said spiral slot portion and subsequently laterally and upwardly into said connector hole portion to hold the tube member therein.

7. An article organizer and holder assembly as described in claim 6, wherein:
(a) an upper portion of said adjacent side walls having a tapered corner section defining a V-shaped groove therewithin operable to initially receive the tube member thereon to provide a guide for moving the tube member downwardly within said spiral slot portion and then laterally and upwardly into said connector hole portion.

8. An article organizer and holder assembly as described in claim 4, wherein:
(a) said spiral slot section of a J-shape having a short leg integral with said said connector hole portion forming a tapered lip portion to enclose and surround an upper portion of the tube member when positioned in said connector hole portion to restrain same from lateral movement upwardly into said spiral slot portion to aid in holding same therein.

* * * * *